United States Patent [19]

Habib

[11] Patent Number: 4,688,554

[45] Date of Patent: Aug. 25, 1987

[54] DIRECTING CANNULA FOR AN OPTICAL DIAGNOSTIC SYSTEM

[75] Inventor: Magdi Habib, Huntington Beach, Calif.

[73] Assignee: American Hospital Supply Corp., Evanston, Ill.

[21] Appl. No.: 850,173

[22] Filed: Apr. 10, 1986

[51] Int. Cl.$^4$ ............................................... A61B 1/00
[52] U.S. Cl. ......................................... 128/4; 604/282
[58] Field of Search ...................... 128/3, 4, 5, 6, 7, 8; 604/280, 281, 282

[56] References Cited

U.S. PATENT DOCUMENTS 3,253,524  5/1966  Ashizawa et al. .................. 128/4 X Primary Examiner—William H. Grieb
Attorney, Agent, or Firm—Perman & Green

[57] ABSTRACT

Apparatus for directing the tip of a scoping instrument having an elongated image transmitting optical system. The elongated optical system is slidably received within the tubular member of a directing cannula mechanism having a bending section at its distal end. The optical system is then held against longitudinal movement relative to the cannula mechanism at a location distant from the distal end. The cannula mechanism can be rotated on its axis for moving the tip of the optical system through 360° of azimuth. A control mechanism is operable from a proximal end of the directing cannula mechanism and includes a single cable which extends through the tubular member to an annular member at the extremity of the distal end. When the desired azimuthal position of the cannula mechanism is achieved the cable is tensioned, enabling the annular member, and with it the tip of the optical system, to be deflected through an arc of 90°, or more.

11 Claims, 9 Drawing Figures

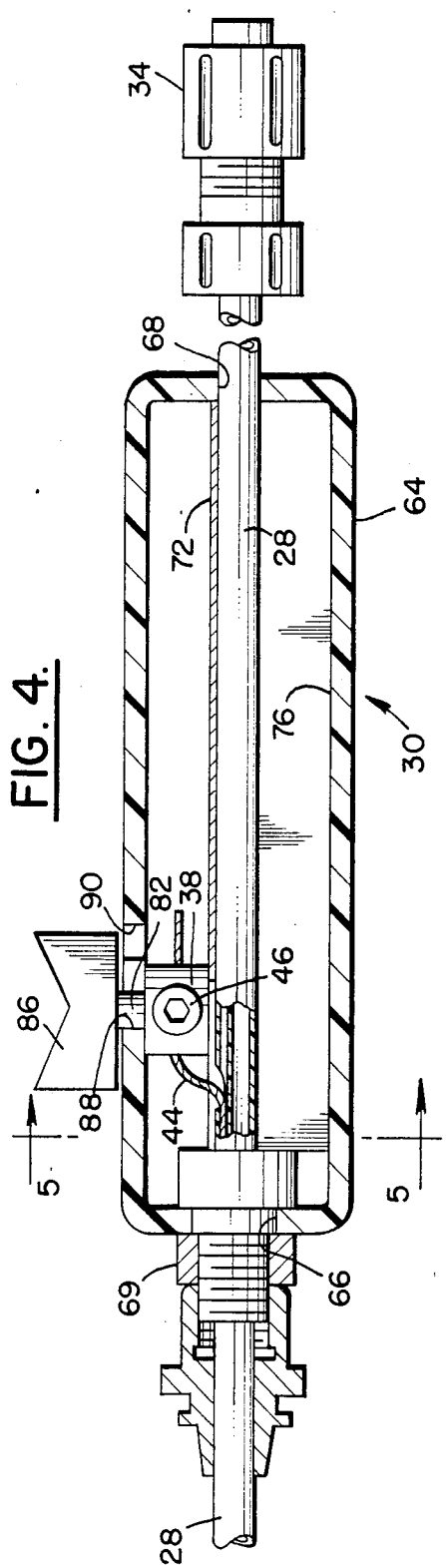
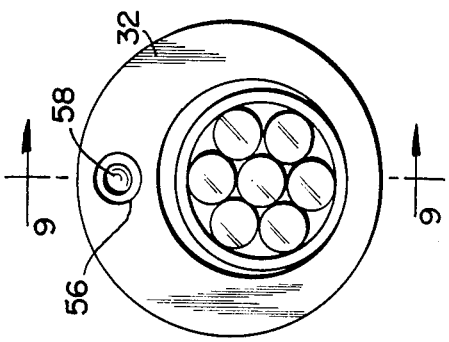
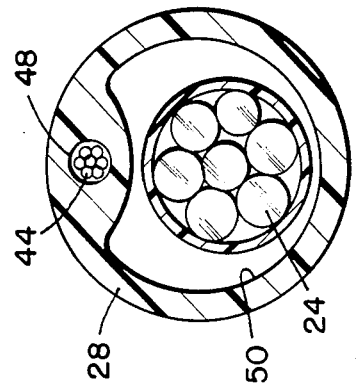
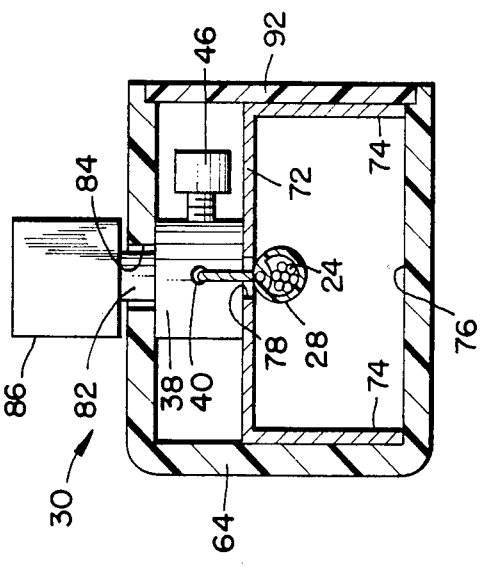

DIRECTING CANNULA FOR AN OPTICAL DIAGNOSTIC SYSTEM

BACKGROUND OF THE INVENTION

The present invention relates generally to endoscopes and, more particularly, to an improved mechanism and the like for controlling the curvature of a bendable portion at the distal end of the endoscope.

In endoscopes of the type which are adapted to be inserted into a body cavity for purposes of diagnosis, treatment, and/or operation of a digestive organ or the like, the bendable portion constituting the distal end of the flexible tubular member which has been inserted into the body cavity must be bent in a controlled manner through external manipulation of components of the endoscope. Difficulties are often encountered however, in manually inserting an endoscope into the digestive tract of a living body. These difficulties chiefly arise from the intricately twisted form of the digestive tract, for example, the large intestine. Therefore, it has hitherto been necessary to try to frequently control the direction in which the distal end portion of an endoscope, for example, a colon scope is inserted into the colon in conformity to the intricately twisted form of the colon in order to effect the smooth full insertion of said instrument. However, the above mentioned control sometimes caused the distal end portion of the endoscope to forcefully press the inner wall of the colon, thus imparting great pain to a patient, and unavoidably prolonging the time of examination.

To alleviate the causes of of pain while enabling a meaningful examination, various mechanisms for controlling the curvature of the bendable portion of the endoscope have been proposed. Many of the known curvature control mechanisms utilize an arrangement wherein a plurality of control wires extend parallel to one another from the forward bendable portion through the flexible tubular member or intermediate portion of the endoscope to a manipulator unit to which the flexible tubular member is attached. The application of a pulling or tension force on one of the control wires results in a tension-relief of another control wire so that a desired curvature of the bendable portion of the endoscope is achieved.

Such devices have also been used for the diagnosis and treatment of disorders associated with joints of the body and notably with the knee joint. For example, American Edwards Laboratories of American Hospital Supply Corporation has developed the Flexiscope ™ System which has served to extend innovative arthroscopic techniques simply, effectively, and with minimal trauma to the patient. The Flexiscope system utilizes an integrated eyepiece with an elongated fiber optic lens system for image and illumination transmission. In brief, after an incision has been made through the skin tissues and into the portions of the joint to be viewed, a tubular introducer is inserted into the joint and attached to the outer tissues covering the joint. Thereafter, a directing cannula is inserted through the introducer into the cavity to be explored. The cannula is of a semi rigid material having a tip end deflected to a predetermined angle relative to the remainder of the cannula. The angle of deflection at the tip end is in the memory of the device such that it can be straightened for passage of the cannula through the introducer, but when the tip end of the cannula emerges from the far end of the introducer, it returns to its predetermined shape. The flexible elongated fiber optic portion of the Flexiscope system is then inserted through the directing cannula down to the tip end and necessarily follows the curvature of the tip end of the cannula. With the tip end of the cannula directed at the object to be examined, the operator of the Flexiscope system can readily view and examine that object.

Presently, a series of directing cannulas is required for purposes of diagnosis, each having a tip end deflected to a different angle of inclination with respect to the major axis of the cannula. These tip ends can typically be bent at a variety of angles between 0° and 90°.

A drawback of this known system becomes apparent when it is desired to examine objects within the joint at different locations or positions. In that event, it is necessary to remove the fiber optic portion of the Flexiscope system as well as the particular directing cannula from the joint cavity, replacing the cannula with one having a different angled tip end, then reinserting the fiber optic portion of the Flexiscope system. This is a laborious, time consuming process which can also cause trauma to the joint structure and possibly pain to the patient.

It was with a view to continuing to use the highly successful Flexiscope system while improving control of the tip end of the fiber optics of that system that the present invention has been conceived and now reduced to practice.

SUMMARY OF THE INVENTION

The invention, then, relates to an apparatus for directing the tip of a scoping instrument having an elongated image transmitting optical system. The elongated optical system is slidably received within the tubular member of a directing cannula mechanism having a bending section at its distal end. The optical system is then held against longitudinal movement relative to the cannula mechanism at a location distant from the distal end. When the cannula mechanism is longitudinally positioned, it can be rotated on its axis at its proximal end for moving a terminal bushing at its distal end through 360° of azimuth to a desired position. Thereupon, a control mechanism is operable from a proximal end of the directing cannula mechanism and includes a single cable which extends through the tubular member to an annular member at the extremity of the distal end. When the cable is tensioned, the annular member, and with it the tip of the optical system, is deflected through an arc of 90°, or more.

By reason of the invention, the operator can use one hand to adjust and manipulate the eyepiece end of the Flexiscope system while using the other hand to operate the control for the tip end in the cavity of the organ being examined. The control mechanism for operating the distal end of the cannula mechanism is aligned therewith, so is readily operable in conjunction with the Flexiscope system. Also, the control mechanism has a provision for enabling the operator to hold the tip of the optical system deflected and held at a predetermined angle. This predetermined angle may be at the maximum angle, at some intermediate angle, or at even a plurality of intermediate angles.

The apparatus which is disclosed herein is of a simplified design resulting in a low initial cost and requiring minimal maintenance. It is of smaller size than conventional devices, and with fewer parts, can be more readily and inexpensively fabricated and assembled.

Indeed, the simplicity of the invention is such that it can be made disposable should that be desired.

Other and further features, objects, advantages, and benefits of the invention will become apparent from the following description taken in conjunction with the following drawings. It is to be understood that both the foregoing general description and the following detailed description are exemplary and explanatory but are not restrictive of the invention. The accompanying drawings, which are incorporated in and constitute a part of this invention illustrate one embodiment of the invention and, together with the description, serve to explain principles of the invention in general terms.

BRIEF DESCRIPTION OF THE DRAWINGS

In the Drawings:

FIG. 4 is a cross section view in elevation, of a control mechanism for the invention;

FIG. 5 is a cross section view taken generally along line 5—5 in FIG. 4;

FIG. 7 is a cross section view taken generally along line 7—7 in FIG. 6;

FIG. 8 is an end elevation view of the tip end of the combination illustrated in FIGS. 1 and 3.

Figure 1:
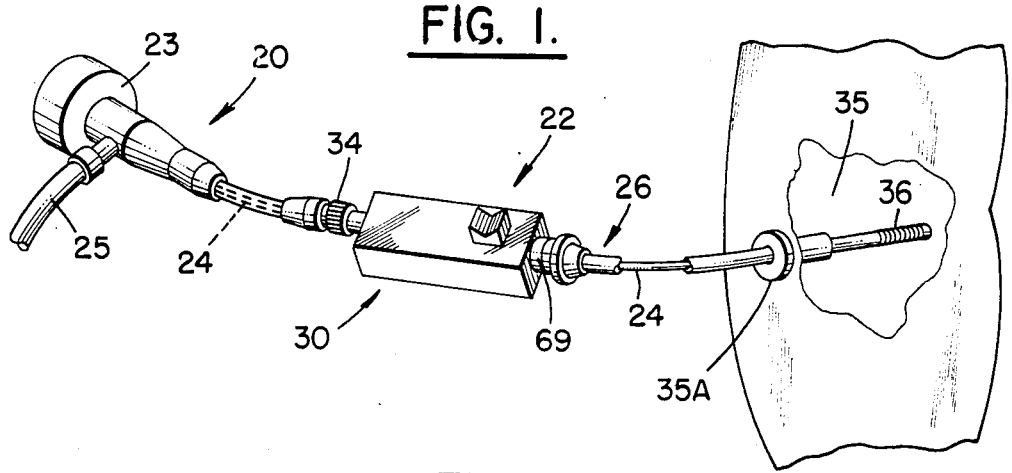
FIG. 1 is a perspective view of the invention utilized in conjunction with a Flexiscope system for the examination of the interior of a body part.

Turn now to the drawings and initially to FIG. 1 which illustrates a scoping instrument 20 used in combination with apparatus 22 of the invention herein. The scoping instrument 20 may be of the type manufactured and sold by American Edwards Laboratories of American Hospital Supply Corporation under the trademark Flexiscope TM or may be of any other suitable type.

As illustrated in FIG. 1, the scoping instrument 20 includes an eyepiece 23, an elongated image transmitting optical system 24, and a light source 25 for transmitting light to the object to be examined in a known manner. While it is preferred that the optical system 24 be of the fiber optical type, it is within the scope of the invention for it to be a conventional hard lens system.

For its part, the apparatus 22 is comprised of a directing cannula 26 which includes a tubular member 28 extending between a distal or extreme end and a proximal end whereat it engages an actuating mechanism 30.

By way of an overview to describe the operation of the invention in general terms prior to describing the details of its construction, the elongated optical system 24 is inserted through the directing cannula 26 until its tip, or extreme, end is generally coextensive with an annular member or distal bushing 32 located at the extreme end of the directing cannula. A suitable clamping device 34 such as that known as a "Toughy Borse" is then tightened so as to hold the optical system 24 against longitudinal movement relative to the directing cannula mechanism 26. The directing cannula mechanism with the elongated optical system 24 therein is inserted into a body cavity 35, (see FIG. 1), such as within a knee joint through an introducer 35A. The introducer is a conventional tubular device which extends through an incision into the cavity 35 and is affixed in a known manner to the outer tissues of the joint.

Figure 3:
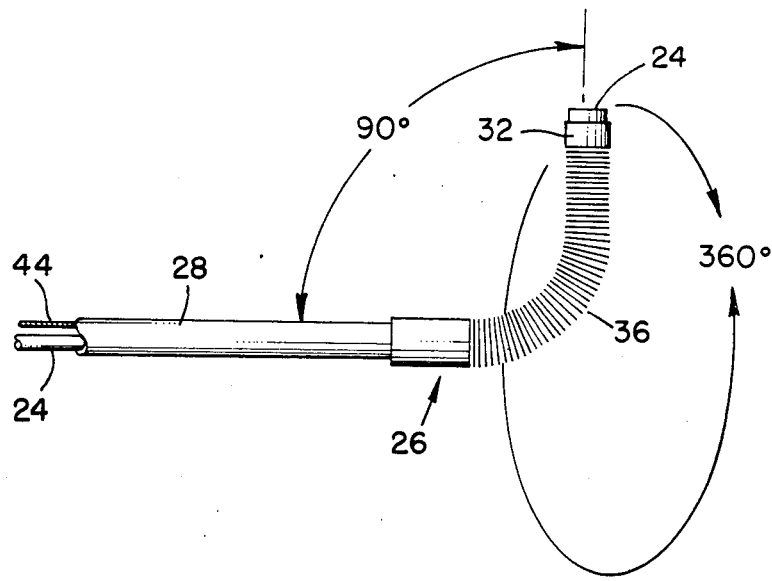
FIG. 3 is a detail side elevation view illustrating a distal end of the invention and diagrammatically illustrating its operation.

The directing cannula 26 includes a bending section 36 which may be in the form of a bellows 36 which normally holds itself and the distal bushing 32 axially aligned with the tubular member 28. However, upon operation of the actuating mechanism in a manner to be described below, the distal bushing 32 and, with it, the tip end of the optical system 24 can be moved to a position angularly disposed relative to the tubular member 28 as illustrated in FIG. 3.

Figure 6:
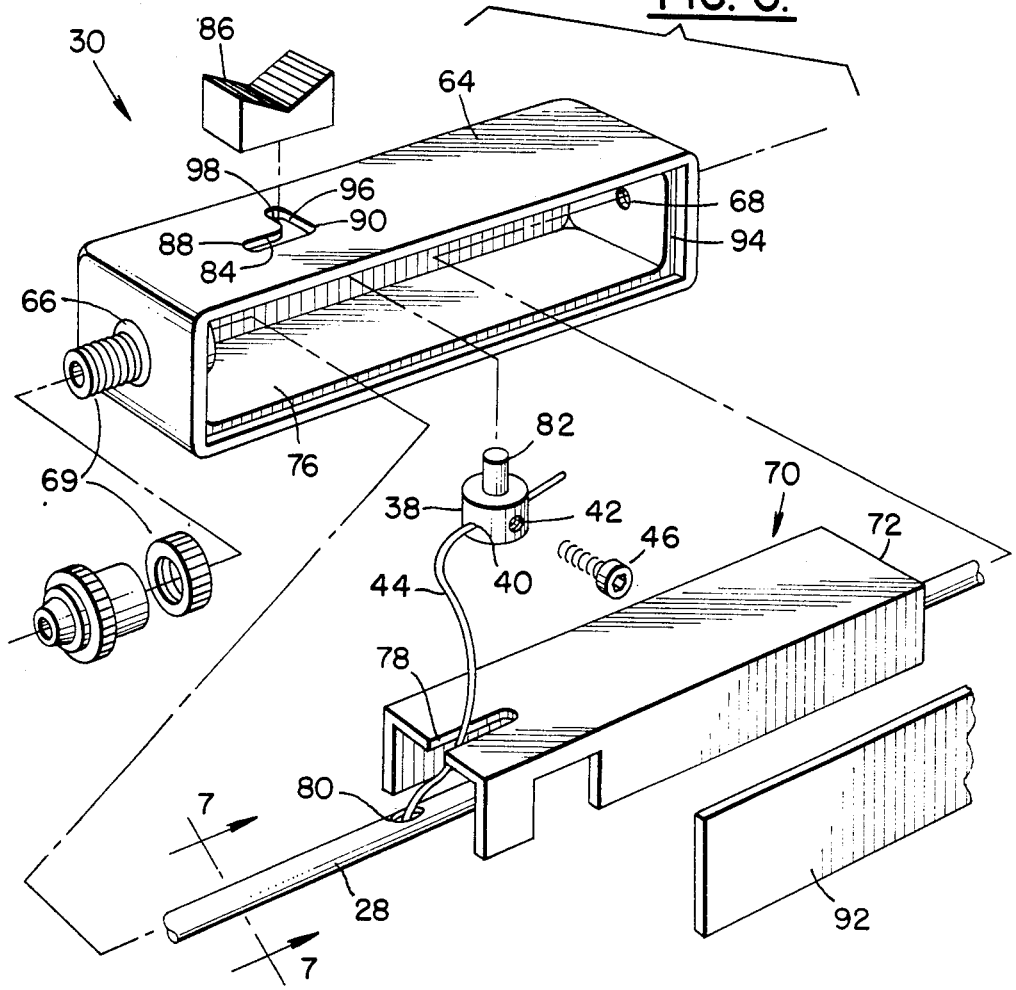
FIG. 6 is an exploded view, in perspective, of the control mechanism illustrated in FIG. 5.

The actuating mechanism 30 is illustrated in detail in FIGS. 4, 5, and 6. As seen in those figures, the actuating mechanism includes an anchor block 38 which is formed with a diammetrically directed bore 40 and a radially tapped bore 42 which communicates with the diammetric bore 40. A proximal end of an operating cable 44 extends through the diammetric bore 40 and is held securely to the anchor block by a set screw 46 threadedly received in the tapped bore 42.

As best seen in FIG. 7, the tubular member 28 is of the double lumen variety having a pair of longitudinal passages 48 and 50 therein. The passage 48 serves to freely receive the operating cable 44 and, similarly, the longitudinal passage 50 serves to freely receive the optical system 24.

Figure 9:
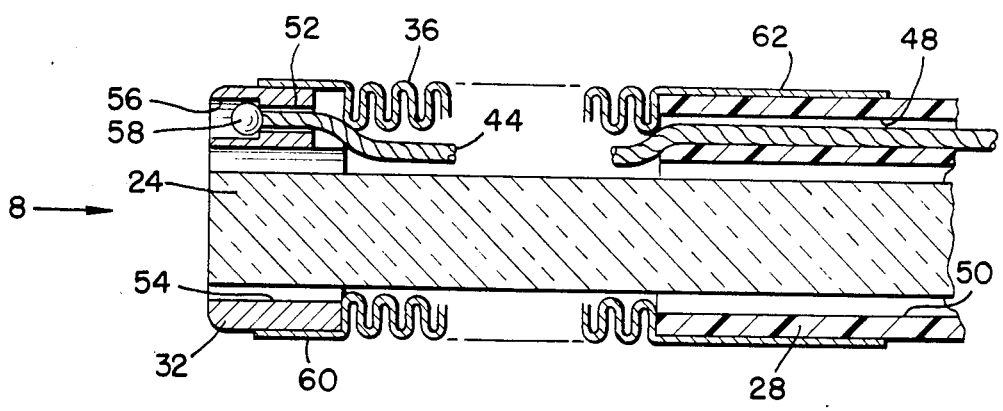
FIG. 9 is a detail cross section view, in elevation, taken generally along the line 9—9 in FIG. 8.

As seen in FIGS. 8 and 9, the terminal bushing 32 is similarly formed with longitudinal passages 52 and 54 corresponding, respectively, to the passages 48 and 50 in the tubular member 28. However, in a surface of the terminal bushing 32 facing away from the actuating mechanism 30, a counterbore 56 is formed at the end of the longitudinal passage 52. An extreme distal end of the operating cable 44 is tig welded to form a ball 58 which is received in the counterbore 56.

As seen in FIG. 9, the bending section 36 is in the form of a bellows which has annular lip portions 60 and 62 at its opposite ends. The lip portion 60 is suitably bonded to the outer surface of the terminal bushing 32 and, similarly, the lip portion 62 is suitably bonded to the tubular member 28. The resulting arrangement of parts as shown in FIG. 9 is such that when the assembly assumes the normal or at rest condition, the tubular member 28, bending section 36, and terminal bushing 32 are all axially aligned.

Turning once again to FIGS. 4, 5, and 6, the remainder of the actuating mechanism 30 will now be described in detail. As the clamping device 34 was previously described as being tightened to hold the optical system against longitudinal movement with respect to the tubular member 28, a generally rectangular shaped housing is slidably received on the tubular member 28 by way of opposed bores 66 and 68 at opposite ends thereof, a similar clamping member 69 serves to hold the housing 64 fixed to the tubular member 28 against both longitudinal movement and rotating movement.

A channel support member 70 is received within the housing 64 and has a web 72 which generally overlies the tubular member 28. Opposed parallel flanges 74 extend downwardly from the web 72 and rest on a floor 76 of the housing 64, The web 72 serves as a support for the anchor block 38 and is formed with a longitudinal notch 78 through which the operating cable 44 can extend. As seen particularly well in FIGS. 4 and 6, the cable 44 extends through a hole 80 in the side wall of the tubular member 28 communicating with the passage 48 which extends therethrough. A guide pin 82, integral with the anchor block 38 and extending upwardly from a top surface thereof extends freely through a longitudinally extending slot 84 formed in an upper wall of the housing 64 and is fixed at its upper end to an actuator button 86.

The operator can move the actuator button 86 along the upper surface of the housing 62, the guide pin 82 following along the length of the slot 84 between a far end 88 and a near end 90 (FIG. 6).

Figure 2:
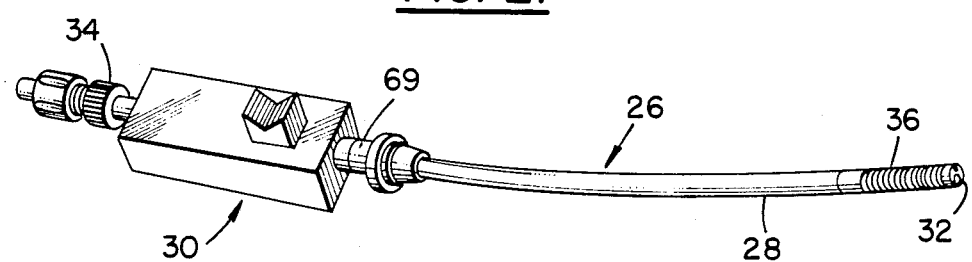
FIG. 2 is a perspective view of the invention.

The length of the operating cable 44 between the ball 58 and the anchor block 38 is so chosen that when the guide pin 82 engages the far end 88 of the slot 84, the distal end of the directing cannula 26 assumes the relaxed position illustrated in FIGS. 2 and 9. However, when the actuator button 86 is moved by the operator towards a proximal end of the directing cannula such that the guide pin 82 engages the near end 90 of the slot 84, the distal end of the directing cannula 26 assumes the deflected position illustrated in FIG. 3 and moves with it the tip end of the optical system 24.

After assembly of the components just described with respect to FIGS. 4, 5, and 6, a cover 92 may be suitably attached to the housing 64 so as to be matingly received on a recessed platform 94, then held in the closed position by suitable means not shown. This serves to protect the internal components of the actuating mechanism 30 from exposure to the environment.

When it is desired to hold the tip end of the directing cannula 26 in the position illustrated in FIG. 3, the actuator button 86 can be laterally moved by the operator, when the guide pin 82 is positioned at the near end 90. When this occurs, the guide pin 82 follows a laterally extending slot 96 which communicates with the longitudinal slot 84. When held in that position, the guide pin 82 can engage a shoulder 98 (FIG. 6) thereby preventing a return of the tip of the directing cannula to the normally at rest condition. It will be appreciated that detent means (not shown) can be utilized to hold the guide pin 82 against the shoulder 96 even when the operator's hand is released from the actuator button 86.

It will also be appreciated that intermediate positions of the distal end of the directing cannula 26 can be effected by operation of the actuator mechanism 30. That is, a full range of movement of the tip end of the directing cannula is achieved according to the positioning of the guide pin 82 along the slot 84. It should also be understood that although the lateral slot 96 as illustrated in FIG. 6 as being at one end of the slot 84, it could also be placed at other longitudinal locations along the slot 84, or, indeed, there could be several lateral slots for desired intermediate positions of the distal end of the directing cannula 26.

To operate the invention, the operator rotates the actuating mechanism 30 on its longitudinal axis, and with it, the directing cannula 26, to thereby move the tip end of the optical system 24 about a 360° arc as illustrated in FIG. 3. When a desired azimuthal position of the directing cannula 26 has been achieved, the distal end of the directing cannula 26 is then deflected to a desired angle from the at rest position. The amount of deflection of the terminal bushing 32 relative to the tubular member 28 can, of course be achieved regardless of the azimuthal position of the directing cannula 26.

Although the invention has been disclosed with a primary use being the diagnosis and treatment of disorders associated with a relatively shallow cavity of the body such as the knee joint, the concept disclosed need not be so limited but can also be employed for deeper elongated body cavities such as the digestive tract. Furthermore, while a preferred embodiment of the invention has been disclosed in detail, it should be understood by those skilled in the art that various modifications may be made to the illustrated embodiment without departing from the scope of the invention as described in the specification and defined in the appended claims.

I claim:

1. Apparatus for directing the tip of a scoping instrument having an elongated image transmitting optical system used for examining internal cavities comprising:
   directing cannula means including:
   a tubular member extending between a proximal end and a distal end adapted to slidably receive therethrough the elongated image transmitting optical system of the scoping instrument such that a terminal end of the optical system is generally coextensive with said distal end of said cannula means; and
   a bending section at said distal end enabling movement of said distal end between a first position axially aligned with said tubular member and a second position angularly disposed relative thereto; and
   actuating means including:
   control means operably disposed on said cannula means adjacent said proximal end thereof and movable between a relaxed position and a fully extended position; and
   a single operating cable fixed at opposite ends, respectively, to said control means and to said distal end of said cannula means;
   whereby movement of said control means between said relaxed position and said fully extended position is effective to move said distal end, and with it, the terminal end of the optical system, between said first position and said second position.

2. Apparatus as set forth in claim 1 wherein said cannula means includes:
   an annular member mounted on said distal end, said bending section having opposed ends mounted, respectively, to said tubular member and to said annular member, said annular member having a distal rim, the terminal end of the optical system being coextensive with said distal rim.

3. Apparatus as set forth in claim 2
   wherein the optical system is a fiber optic bundle;
   said apparatus including holding means selectively applied at a location distant from said distal end to prevent relative axial movement of the fiber optic bundle and the tubular member when the terminal end of the optical system in coextensive with said distal rim.

4. Apparatus as set forth in claim 1
   wherein said tubular member has first and second passages extending therethrough;
   said first passage adapted to receive therein said cable and said second passage adapted to receive therein the optical system.

5. Apparatus as set forth in claim 4
   wherein said tubular member has a hole in its sidewall communicating with said first passage adjacent said proximal end, said cable adapted to extend through the hole;
   wherein said actuating means includes a support member; and
   wherein said control means includes:

anchor means external of said tubular member adjacent said proximal end affixed to said cable, said anchor means being movable on said support member between said relaxed position and said fully extended positions.

6. Apparatus as set forth in claim 4 wherein said tubular member has a hole in its sidewall communicating with said first passage adjacent said proximal end, said cable adapted to extend through the hole; and wherein said actuating means includes;

a housing mounted on the exterior of said tubular member coextensive with the hole therein and having a longitudinal slot therethrough between a near end and a far end;

a support member within said housing;

an anchor block affixed to said cable slidably mounted on said support member for movement longitudinally of said tubular member between said relaxed position and said fully extended position;

an actuator button; and a guide pin having ends fixed respectively to said anchor block and to said actuator button and extending freely through the slot in said housing.

7. Apparatus as set forth in claim 6 wherein said anchor block is at said relaxed position when said guide pin engages the far end of the slot and is at said fully extended position when said guide pin engages the near end of the slot; and wherein the slot has a transversely extending portion at the near end thereof defining a shoulder engageable by said guide pin for selectively holding said anchor block at said fully extended position.

8. Apparatus as set forth in claim 2 wherein said tubular member has first and second passages extending therethrough, said first passage adapted to receive therein said cable and said second passage adapted to receive therein the optical system; and wherein said annular member has first and second passages extending therethrough aligned, respectively, with said first and second passages of said tubular member when said annular member assumes said first position axially aligned with said tubular member, said first passage of said annular member adapted to receive therein said cable and said second passage of said annular member adapted to receive therein the optical system.

9. Apparatus as set forth in claim 8 wherein said cable has an enlarged ball fixed to a distal end thereof; and wherein said annular member has a counterbore in its surface distant from said tubular member, the counterbore being axially aligned with said first passage therein and adapted to receive said enlarged ball therein.

10. Apparatus as set forth in claim 9 wherein said tubular member has a hole in its sidewall communicating with said first and second passage therein adjacent said proximal end, said cable extending through the hole; and wherein said actuating means includes:

a housing mounted on the exterior of said tubular member coextensive with the hole therein and having a longitudinal slot extending therethrough between a near end and a far end; and a support member within said housing;

an anchor block affixed to said cable slidably mounted on said support member for movement longitudinally of said tubular member between said relaxed position and said fully extended position;

an actuator button; and a guide pin having ends fixed respectively to said anchor block and to said actuator button and extending freely through the slot in said housing.

11. Apparatus as set forth in claim 10 wherein said anchor block is at said relaxed position and said annular member is at said first position when said guide pin engages the far end of the slot, and said anchor block is at said fully extended position and said annular member is at said second position when said guide pin engages the near end of the slot; and wherein the slot has a transversely extending portion at the near end thereof defining a shoulder engageable by said guide pin for selectively holding said anchor block at said fully extended position.

* * * * *